US010201292B2

(12) United States Patent
Sharpe et al.

(10) Patent No.: US 10,201,292 B2
(45) Date of Patent: Feb. 12, 2019

(54) ACTIVITY MONITORS

(71) Applicant: Speedo International Limited, London (GB)

(72) Inventors: Tim Sharpe, Nottingham (GB); Depal Patel, Nottingham (GB); Chris Johnson, Nottingham (GB)

(73) Assignee: SPEEDO INTERNATIONAL LIMITED, London (GB)

( * ) Notice: Subject to any disclaimer, the term of this patent is extended or adjusted under 35 U.S.C. 154(b) by 509 days.

(21) Appl. No.: 14/657,554

(22) Filed: Mar. 13, 2015

(65) Prior Publication Data

US 2015/0305655 A1 Oct. 29, 2015

(30) Foreign Application Priority Data

Apr. 25, 2014 (GB) .................... 1407288.8

(51) Int. Cl.
*A61B 5/11* (2006.01)
*G09B 19/00* (2006.01)
(Continued)

(52) U.S. Cl.
CPC .............. *A61B 5/1118* (2013.01); *A41D 7/00* (2013.01); *A61B 5/1123* (2013.01); *A63B 69/12* (2013.01); *G09B 19/0038* (2013.01); *A61B 5/1116* (2013.01); *A61B 2503/10* (2013.01); *A61B 2560/0209* (2013.01); *A61B 2560/0242* (2013.01); *A61B 2560/0406* (2013.01); *A61B 2562/0219* (2013.01); *A63B 2220/803* (2013.01); *A63B 2220/836* (2013.01); *A63B 2244/20* (2013.01); *G01S 19/19* (2013.01)

(58) Field of Classification Search
None
See application file for complete search history.

(56) References Cited

U.S. PATENT DOCUMENTS

| 4,776,045 A | 10/1988 | Mysliwiec et al. |
| 8,265,900 B2 | 9/2012 | Irlam et al. |

(Continued)

FOREIGN PATENT DOCUMENTS

| GB | 2509945 | 7/2014 |
| JP | 2007-229416 | 9/2013 |
| TW | 201404436 | 2/2014 |

OTHER PUBLICATIONS

Search Report Under Section 17(5) for Great Britain Application No. GB1407288.8, dated Sep. 30, 2014, Intellectual Property Office, South Wales, Great Britain.
(Continued)

*Primary Examiner* — Tung S Lau
(74) *Attorney, Agent, or Firm* — Marvin Petry; Stites & Harbison PLLC (57) ABSTRACT

An activity monitor that is worn by a user for monitoring water-based activities. The activity monitor includes at least one motion sensor, a water sensor, a memory, and a processor. The processor is operable to run an algorithm to calculate activity data based on an output from the motion sensor and to save the activity data to the memory. The processor can be triggered to operate to calculate the activity data and to save it to memory by an output from the water sensor to indicate that the monitor is immersed in water.

10 Claims, 9 Drawing Sheets

(51) Int. Cl.
*A41D 7/00* (2006.01)
*A63B 69/12* (2006.01)
*G01S 19/19* (2010.01)

(56) References Cited

U.S. PATENT DOCUMENTS

| | | |
|---|---|---|
| 2006/0098772 A1 | 5/2006 | Reho et al. |
| 2007/0293374 A1 | 12/2007 | Chan |
| 2010/0030482 A1 | 2/2010 | Li |
| 2012/0118084 A1 | 5/2012 | Klose et al. |
| 2014/0059365 A1 | 2/2014 | Heo et al. |
| 2014/0197963 A1* | 7/2014 | Park ................. G08B 21/18 340/870.01 |

OTHER PUBLICATIONS

Extended European Search Report for Great Britain Application No. 15160239.8, dated Sep. 24, 2015, European Patent Office, Munich, Germany.

* cited by examiner

ACTIVITY MONITORS

FIELD OF THE INVENTION

The invention relates to activity monitors and in particular to devices that are worn by a user for monitoring water-based activities.

BACKGROUND

Swimming is a popular competitive sport and, especially for athletes competing at the higher levels, significant investment is made to track their training and competitive races to collect data that can be used to monitor and help improve their performance.

There are also very many people that, although not participating at a competitive level, swim regularly to maintain or improve their fitness and general wellbeing. In the past, this type of swim 'consumer' has not been especially concerned with monitoring their performance. More recently, however, there has been a growing trend for consumers to measure and capture data around many aspects of their life, typically using a smartphone (sometimes in combination with ancillary motion sensors), especially for diet and fitness activities. Capturing such "personal metrics" enables a consumer to more easily understand their performance and seek to maintain or improve performance through the setting and tracking goals for their fitness activities.

Whilst developments in recent years now means there are a wide range of activity monitors available to the consumer for monitoring land-based activities (walking, running, cycling, etc), the development of activity monitors for water-based activities (swimming, water-aerobics, water-polo, underwater hockey, etc) has been less rapid, in part down to the unique challenges faced in capturing and recording data during water-based activities, especially the need to ensure that monitoring devices can function reliably when immersed in water.

One example of a known swim activity monitor is the Speedo Aquacoach™ watch. This waterproof watch can be worn by a swimmer in the pool and can be used to track laps, distance, speed and calories burned. It also detects swim stroke per lap utilising an inbuilt accelerometer. US2010-0030482 describes another example of a swim activity monitor. The monitor described in this document measures body orientation and forward speed with a three axis accelerometer (and optionally also a three axis gyroscope) that is worn by the swimmer on the small of their back, abdomen or head. This monitor provides real-time feedback to the swimmer via an earpiece or a swimming goggle with a digital display.

Another type of activity monitor that can be used during swimming is a multi-activity monitor. That is, a monitor that can operate to record multiple different type of activity (e.g. running, walking, cycling and swimming), such as the Fitbit™ activity trackers. Another example of a multi-activity monitor is described in US2012/0118084. The monitor described in this document records movement and automatically switches between a mode for operating in air and a mode for operating in water, i.e. swimming, using a sensor that determines when the monitor is in water.

One problem with known activity monitors, especially those using complex algorithms to determine, for example, different types of motion, is that the on-board processing of the algorithm quickly depletes a battery. This leads to monitors that are either bulky to incorporate high capacity batteries or that require fairly frequent changes of batteries (e.g. every 2 or 3 months) or frequent recharging. A compact swim monitor with a long battery life (for example, up to a year or more, would be desirable).

SUMMARY OF INVENTION

A general aim of the present invention is to provide an improved activity monitor for monitoring water-based activity.

Accordingly, in a first aspect the invention provides an activity monitor for water-based activity, the activity monitor adapted to be worn by a user to monitor a water based activity performed by the user, the monitor comprising:
  at least one motion sensor;
  a water sensor;
  a memory; and
  a processor operable to run an algorithm to calculate activity data based on an output from the at least one motion sensor and to save the activity data to the memory;
  wherein the processor can be triggered to operate to calculate the activity data and save it to memory by an output from the water sensor to indicate that the monitor is immersed in water.

Activity monitors in accordance with this first aspect of the invention potentially have much longer battery life than might otherwise be the case because the duration for which the processor is operating in a relatively high power consumption state to perform the activity data calculations is restricted to periods of time when the activity monitor (and hence the user) is actually in the water (without the need for user intervention).

In some examples of this first aspect of the invention, the processor only operates to calculate the activity data and save it to memory when, in addition to an output from the water sensor indicating that the monitor is immersed in water, an output from the motion sensor or from an additional activity sensor indicates that the user is performing an activity. This further minimises the time during which the processor is consuming batter power to calculate activity data. It can avoid, for example, the active mode being triggered when the user is showering before entering a pool.

For example, in the case where the activity monitor is for measuring a swimming activity, the relevant output from the motion sensor or from an additional activity sensor may be one that indicates the orientation of the user in the water, the processor only operating to commence calculation of the activity data when the sensor indicates the user's orientation to be substantially horizontal Similarly, the processor may be programmed to stop calculation of the activity data when the output from this sensor indicates that the user is in an upright orientation (even if the activity monitor is still immersed). Additionally or alternatively, in some examples, the processor only operates to calculate the activity data and save it to memory when an output from the motion sensor indicates that the user is moving.

In embodiments of the invention, the at least one motion sensor may be one or more of an accelerometer, a gyroscope, a digital compass and a GPS receiver. The activity monitor may include a combination of two or three or more of these motion sensors, for example to improve its capability to distinguish different types of motion and accuracy of lap counts.

In some embodiments, the activity monitor has a sleep mode in which the monitor consumes little or no battery power (e.g. less than 5 uA, preferably less than 3 uA and more preferably 1 uA or less), a standby mode in which power consumption is higher than the sleep mode (typically about 10 uA to 15 uA) but in which the processor is not operating to calculate activity data and an active mode in which the processor is operating to calculate activity data. In the active mode the power consumption will likely be 30 uA or more, typically around 50 uA, with (momentary) peak consumption up to 150 uA or more. The monitor may be configured so that it cannot switch directly from sleep mode to active mode, even if the water monitor is immersed in water. In this way, a user can better ensure that the monitor is not inadvertently activated when not intended.

In some embodiments the monitor further comprises a wireless transmitter for transmitting activity data from the memory to another device, such as a smartphone or other computing device. The wireless transmitter may be a wireless transceiver so that the activity monitor can also receive data from another device. One appropriate form of wireless transmission is Bluetooth.

In a second aspect, the invention provides an activity monitor for water-based activity, the activity monitor adapted to be worn by a user to monitor a water based activity performed by the user, the monitor comprising:
at least one motion sensor;
a memory;
a battery to power the monitor; and
a processor operable to run an algorithm to calculate activity data based on an output from the at least one motion sensor and to save the activity data to the memory;
wherein the monitor has a sleep mode in which the monitor consumes little or no battery power, a standby mode in which power consumption is higher than the sleep mode but in which the processor is not operating to calculate activity data and an active mode in which the processor is operating to calculate activity data;
the activity monitor being responsive to a first trigger to switch from sleep mode to standby mode and responsive to a second, different trigger to switch from standby mode to active mode.

By providing a sleep mode in addition to a standby mode it is possible to have a device that requires two triggers for activation, one of which can for example be user initiated and the other automatic.

Automatic on/off triggers for an activity monitor can be useful as they avoid having to rely on a user remembering the trigger the activity monitor in advance of commencing an activity, whilst allowing the monitor to revert to a lower power consumption standby mode between periods of activity. User initiated triggers, on the other hand, allow the user to ensure that power consumption is minimal (or preferably zero) during periods when they know that the activity monitor will not be used. The sleep and standby modes proposed here, with separate triggers, can offer the benefits of both automatic triggers and manually initiated triggers.

In some embodiments the first trigger is a physical interaction by a user with the monitor. It may, for example, be the user shaking the monitor or manipulating (e.g. pressing, sliding, etc) a button on the monitor.

Alternatively, the first trigger may be a wireless signal from another device, for example a signal from a smartphone or other computing device (that the user or another person operates) or a signal from a wireless beacon in a particular geographical location, so that the activity monitor is switched from sleep to standby mode automatically when in proximity to that location.

In some embodiments the second trigger may comprise an output from a water sensor that indicates that the monitor is immersed in water.

In a third aspect, the invention provides a swimsuit in combination with an activity monitor mounted on the swimsuit, wherein:
the swimsuit comprises a first attachment feature at a predefined location on the suit; and
the activity monitor comprises a second attachment feature that cooperates with the first attachment features to mount the activity monitor on the swimsuit at said predefined location.

This approach ensures that the activity monitor can be reliably located at the same position on the swimsuit whenever it is used, which helps to ensure consistency between measurements taken in different activity sessions.

In some embodiments the first and second attachment features are adapted to mount the activity monitor at said predefined location on the swimsuit in a specific orientation. This can be important, for example, when the activity monitor includes a motion sensor such as an accelerometer, the output of which is sensitive to orientation.

In some embodiments the pre-defined location corresponds to a mid-line of a user's torso when they wear the swimsuit. This position has been found to allow more reliable detection of various forms of movement of the user, in particular stroke type for a swimmer. The activity monitor may, for example be located on the mid-line of the back of the swimsuit. One location that has been shown to be particularly appropriate (e.g. to detect stroke type for a swimmer) when using a single activity monitor is the small of the user's back. Especially in cases where multiple monitors are used, other locations may be more appropriate.

In some embodiments the activity monitor is replaceably removable from the swimsuit. That is to say, it can be removed from the swimsuit and then later replaced at the same location by virtue of the corresponding attachment features.

Various suitable forms of corresponding attachment features may be used. For example the first feature may be a pocket in the swimsuit that is configured to receive the activity monitor and the second feature may be a housing of the activity monitor that is shaped to be received in the pocket.

In another example, the first feature may be a slot in the swimsuit or a loop on the swimsuit and the second feature may be a clip on the activity monitor that engages the slot or loop. In a further example, the first feature may be a graphical marker on the suit to indicate a location for the activity monitor and the second feature may be a shape of the activity monitor housing or a graphical marker on the activity monitor to align with the marker on the suit. In this latter example (and in other examples) the activity monitor may be attached to the suit by a magnet or magnets.

As an alternative to being replaceably removable from the swimsuit, the activity monitor may be integrated with the swimsuit. For example, it may be secured in a pocket in the swimsuit that is stitched or bonded closed or the activity monitor may be woven into the suit.

As in embodiments of the other aspects above, the activity monitor may be configured so that when it is immersed in water it switches into an active mode in which it captures activity data.

The activity monitor in the combination of this third aspect may be an activity monitor in accordance with the first and/or second aspect above and may incorporate any one or more of the features discussed above in the context of those aspects.

In some embodiments, as already alluded to above, a swimsuit may be provided with a plurality of activity sensors mounted at a corresponding plurality of predefined locations.

In a fourth aspect, the invention provides a swimsuit for use with a swimsuit and activity monitor combination according to the third aspect, the swimsuit comprising at least one attachment feature at a predefined location on the swimsuit adapted to receive an activity monitor.

In a fifth aspect, the invention provides a method for recording water-based activity of a person using an activity monitor mounted on the person's body, the activity monitor having a sleep mode in which the monitor consumes little or no battery power, a standby mode in which power consumption is higher than the sleep mode but in which the processor is not operating to calculate activity data and an active mode in which the processor is operating to calculate activity data, the method comprising:
  triggering the activity monitor to switch from the sleep mode to the standby mode;
  when in the standby mode, the activity monitor automatically switching from the standby mode to the active mode when the activity monitor is immersed in water; and
  when in the active mode the activity monitor automatically switching from the active mode to the standby mode when the activity monitor is no longer immersed in water.

In some embodiments, the activity monitor switches from the standby mode to the active mode only when the activity monitor is immersed in water and the activity monitor determines that an activity has commenced. The activity monitor may determine that an activity has commenced based, for example, on a detected orientation of the person in the water and/or a detected movement of the person in the water.

The activity data may be recorded in a memory in the activity sensor when the activity sensor is in the active mode and, after the activity monitor has switched from the active mode to the standby mode, transmitted from the activity monitor to a computing device. In this way, the activity monitor need not include an interface for viewing the data, which can later be viewed on the computing device. This approach also means that the computing device need not be kept in close proximity to the activity monitor whilst the activity monitor is recording data, which may not be practical during water-based activities.

The data may be transmitted wirelessly, for example using a Bluetooth wireless connection. The computing device may be a smartphone.

Once the data is received at the smartphone (or other computing device) it may be viewed. It may also be transmitted to another remote computer over the Internet for example.

In some embodiments of this aspect, the method includes prior to commencing their water-based activity the person using the computing device (e.g. smartphone) to set one or more goals so that after their activity has stopped and the recorded activity data has been transmitted to the computing device, the recorded activity data may be compared with the goals that were set.

As noted above, it has been found that an activity monitor, for example a monitor in accordance with the first or second aspect above, mounted on the mid-line of a swimmer's torso (especially in the small of their back) can be particularly well suited to detecting stroke type (e.g. distinguishing between front crawl, breaststroke, backstroke and butterfly).

In a sixth aspect, the invention provides an activity monitor for monitoring swimming activity, the activity monitor adapted to be worn by a user on the mid-line of the user's torso to monitor a swimming activity performed by the user, the monitor comprising:
  at least one motion sensor; and
  a processor operable to run an algorithm to calculate stroke type based on an output from the at least one motion sensor.

The invention also provides a combination of a swimsuit and an activity monitor in accordance with the sixth aspect mounted on the swimsuit at a location that corresponds to the mid-line of a user's torso when the swimsuit is worn. In some embodiments the activity monitor is located on the back of the swimsuit, for example at a position that corresponds to the small of the user's back when the swimsuit is worn.

BRIEF DESCRIPTION OF THE FIGURES

An embodiment of the invention is described below by way of example with reference to the accompanying figures, in which:

FIGS. 9(a) to 9(d) illustrate a method of using an activity monitor, in accordance with an embodiment of the invention, to capture activity data during a swimming session wherein FIGS. 9(a) to 9(d) depict a single chart taken from left to right respectively.

DESCRIPTION OF EMBODIMENTS

Embodiments of the invention are described below in the context of monitoring swimming activity.

It will be appreciated, however, that the same of similar activity monitors could be used to monitor other water-based activities in a similar way.

Figure 1:
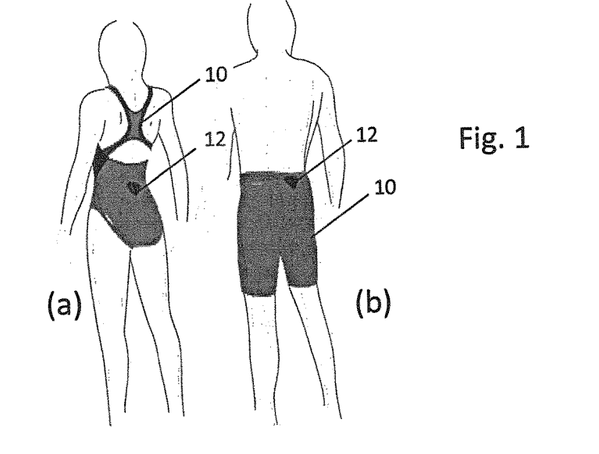
FIG. 1 schematically shows two examples of an activity monitor mounted on a swimsuit in accordance with an embodiment of the present invention.

FIG. 1 shows two exemplary swimsuits 10, one female (a) and one male (b), that incorporate swimming activity monitors 12 in accordance with embodiments of the invention. In these examples, each suit has a single activity monitor 12 mounted on the suit 10 at a location that approximates to the small of the swimmer's back when the suit is worn. The activity monitor is small (for example no more than about 45 mm long and 30 mm wide) and low profile (for example, no more than about 12 mm deep) so that it can be mounted on the swimsuit in an unobtrusive way that does not interfere with the swimmer's activity and in particular does no appreciably increase drag in the water. In these examples, the monitors are securely held in place in a pocket in the swimsuit, the shape of the housing of the monitor and the shape of the pocket cooperating to hold the monitor in a predefined orientation.

The activity monitor used to calculate and record activity data during swimming sessions that can subsequently be uploaded to another device (for example a smartphone, Internet connected computer, etc) for later viewing and analysis.

The activity monitor itself is a self-contained device that, in these examples, can be removed from and replaced in the pocket in the swimsuit. In other examples, the device may be permanently attached to the swimsuit. The monitor preferably includes a water tight housing within which all of the electronic device components are retained. The outside of the housing may be shaped to fit snugly into a pocket in the swimsuit, as in these examples, or may comprise further attachment features to secure the device to the swimsuit (some examples of which are discussed further below).

Preferably the monitor floats in water so that if it inadvertently becomes detached from the swimsuit it is easier to retrieve. It is also preferred that the monitor housing, as well as providing a waterproof container for the monitor electronics, is made of a material that is resistant to the environments it is likely to be used, including chlorinated swimming pools and open fresh and sea water. The monitor is preferably compliant with International Protection Marking IP67 (protection when immersed in water to a depth of 1 m) and more preferably IP68 (immersed in water to a depth of beyond 1 m).

Some embodiments may be operable up to depths of 50 m, 100 m or more.

Figure 2:
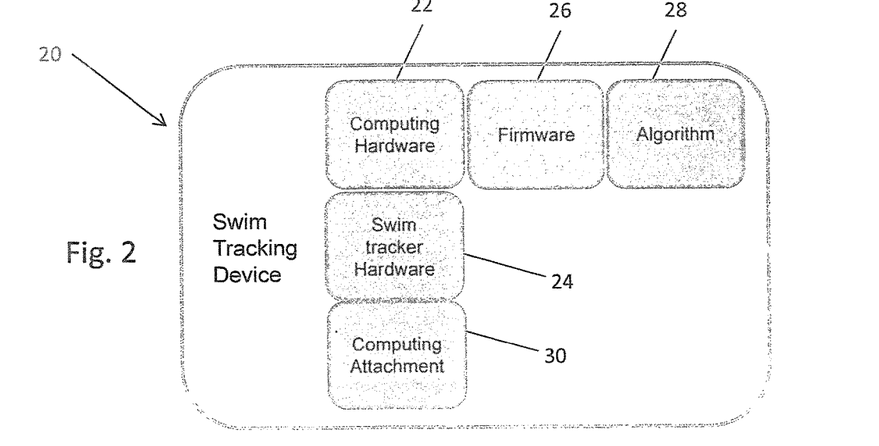
FIG. 2 schematically shows the main components of an activity monitor in accordance with an embodiment of the present invention.

FIG. 2 schematically shows the main components of the swimming activity monitor 20. The swim tracking device 22 will include a battery, one or more motion or activity sensors and a water sensor.

The battery preferably has a capacity that means the batter can power the device for at least 1 year of 'typical use'. 'Typical use' is assumed to be 6 hours use per week including 4 separate data uploads per week. The monitor may be designed to allow batter replacement so that it can be replaced once the batter is exhausted, so long as this is done in a way that can ensure the waterproofness of the device subsequent to battery replacement. Alternatively, the device may be disposable in the sense that once the battery is exhausted the device is disposed of and a new device acquired. It is also possible to use a rechargeable battery that can be recharged with a wired (e.g. mini-usb) of wireless (e.g. induction charging) method.

The motion/activity sensor may be one or more of an accelerometer, a gyroscope, a GPS receiver, or other sensor capable of detecting motion or more generally activity of the swimmer.

Any suitable water sensor may be used. It may, for example, be a capacitive sensor in which the capacitance of a conductive element is measured to determine whether the element is immersed.

The element may, for example, be a conductive pad bonded to the case of the activity sensor.

Alternatively, the water sensor may be a resistive sensor that uses a pair of conductive contacts with faces exposed to the exterior of the activity monitor housing, the resistance across the two contact being measured to determine whether or not they are immersed. The water sensor detects when the activity monitor is immersed and an output from this senor is used to restrict operation of the monitor to record activity data to periods of time when the monitor is immersed.

The computing hardware 24 includes a processor and a memory for storing activity data generated by an algorithm executed by the processor. Preferably at least 4 hours of swimming data can be stored. The firmware 26 comprises operating code and the algorithm 28 stored in persistent memory. The computing hardware also includes a Bluetooth transceiver for sending and receiving data, for example to enable upload of the stored activity data from the memory to another computing device (e.g. a smartphone).

In use, the processor receives inputs from the motion/activity sensor(s) and the water sensor and executes the algorithm to calculate activity data from these inputs. The activity data includes one or more of speed, laps, distance, time, stroke type, stroke count, stroke efficiency (strokes per lap) and calories.

The activity monitor preferably has three modes: a sleep mode (in which very little or no batter power is consumed); a standby mode from in which the processor is not operating to calculate activity data; and an active mode in which the processor is operating to calculate activity data. The monitor switches automatically from the standby mode to the automatic mode based on an output from the water sensor—when the water sensor is immersed the monitor switches from standby mode to active mode. When the water sensor detects that the monitor is no longer immersed, the monitor is switched from active mode back into standby mode. The monitor may then return to sleep mode after a pre-determined period of time has elapsed following switching back to standby mode (e.g. 30 mins) and/or a predetermined period of time after the at wireless data connection is terminated. In another example, the automatic switching from standby mode to active mode may also be dependent on an output from a motion/activity sensor so that the recording of activity data only commences when water-based activity has actually commenced and is not triggered, for example, when the user showers before entering the pool. This may be achieved, for example, by using a sensor that detects when the user's orientation and keeps the monitor in standby mode when the user is upright even if the monitor is immersed in water.

The attachment 30 of the activity monitor to the suit is achieved by cooperating attachment features on the suit and device. It is important that the attachment holds the device securely to the swimsuit in a fixed position (and preferably also orientation) because if the device moves significantly relative to the swimmer's body during exercise then the output from the motion sensor is unlikely to correctly reflect the motion of the swimmer in the water. Likewise, if the position (and orientation) of the monitor (and in particular the motion sensor within it) cannot be suitably repeated from one swim session to the next, then it becomes difficult or impossible to compare data from different session, which is desirable to monitor progress in performance over time.

FIGS. 3 to 8 show several examples of possible features for attaching the activity monitor to the swimsuit.

Figure 3:
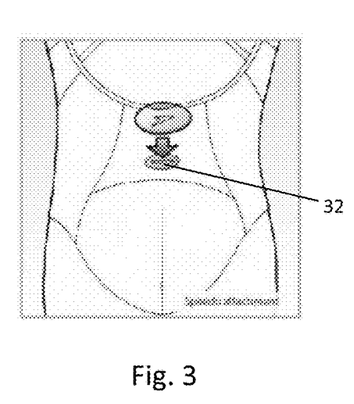
FIGS. 3 to 8 illustrate several possible ways in which an activity monitor can be mounted on a swim suit in accordance with embodiments of the invention.

FIG. 3 shows a slot 32 formed in the back of the swimsuit in to which a clip (not shown) on the activity monitor can be secured. A similar fixture can be achieved with a loop on the back of the swimsuit to which the monitor can be clipped.

Figure 4:
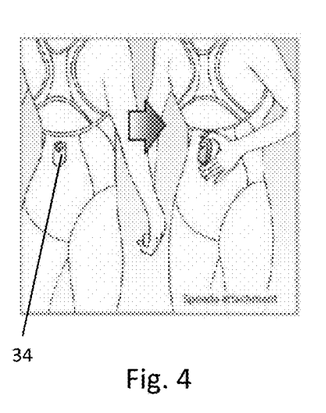

FIG. 4 shows a magnetic clip attachment 34.

Figure 5:
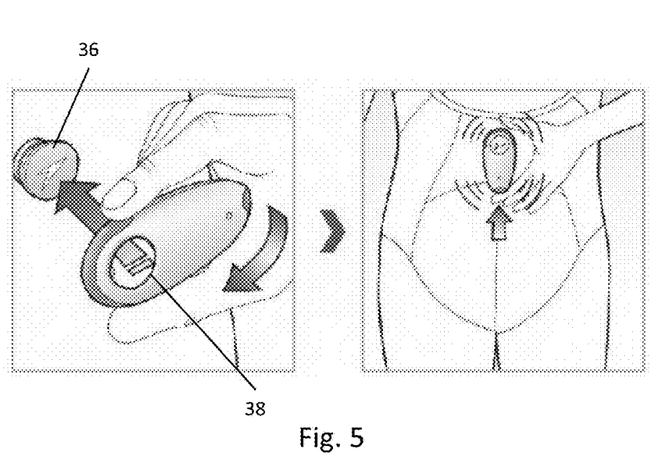

FIG. 5 shows an attachment arrangement that includes a protruding button 36 on the back of the swimsuit that engages with an opening 38 in the housing of the monitor.

Figure 6:
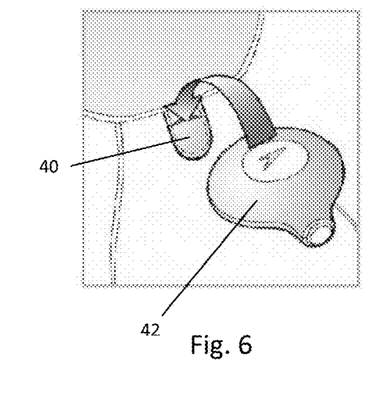
Figure 7:
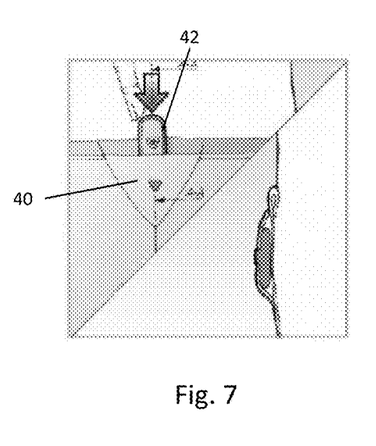
Figure 8:
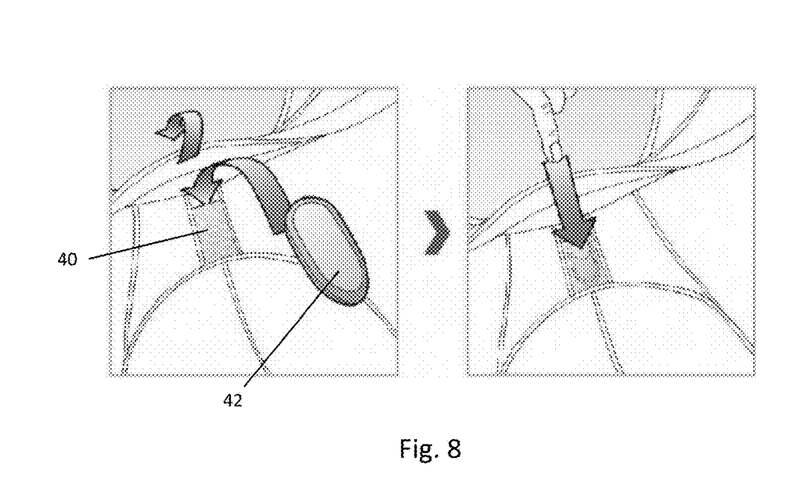
Figure 10:
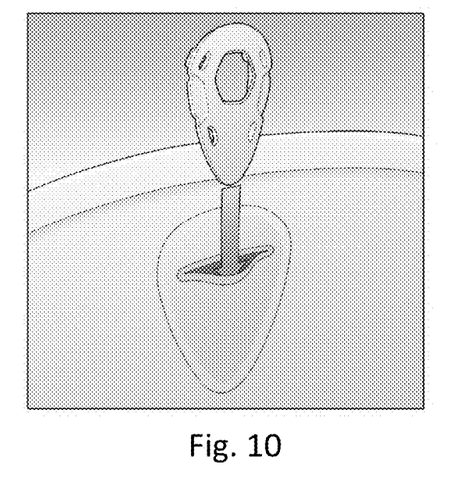
FIGS. 10-12 illustrate further exemplary ways in which an activity monitor can be mounted on a swim suit in accordance with embodiments of the invention.
Figure 11:
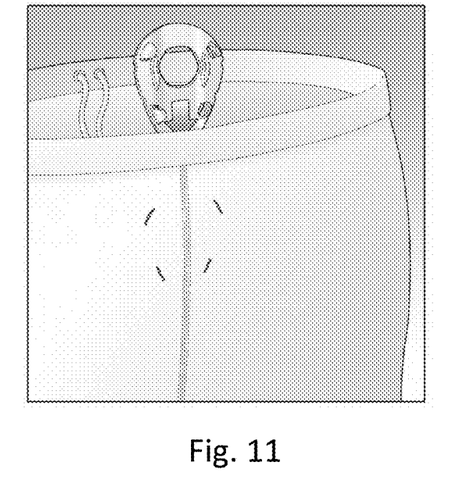

FIGS. 6, 7 and 8 show alternative attachment arrangements that all use a pocket 40 in the swimsuit into which the activity monitor 42 is received. By appropriate design of the shape of the pocket and the exterior shape of the activity monitor housing it is possible to securely locate the monitor in a specific orientation and position on the swimsuit. FIGS. 10 and 11 show a further example of an arrangements in which the activity monitor is secured in a pocket in a swimsuit. In the case, the pocket is on the inside of the swimsuit, FIG. 10 showing the inside surface of the swimsuit, with the pocket, and FIG. 11 showing a view from the outside of the back of the swimsuit.

Figure 12:
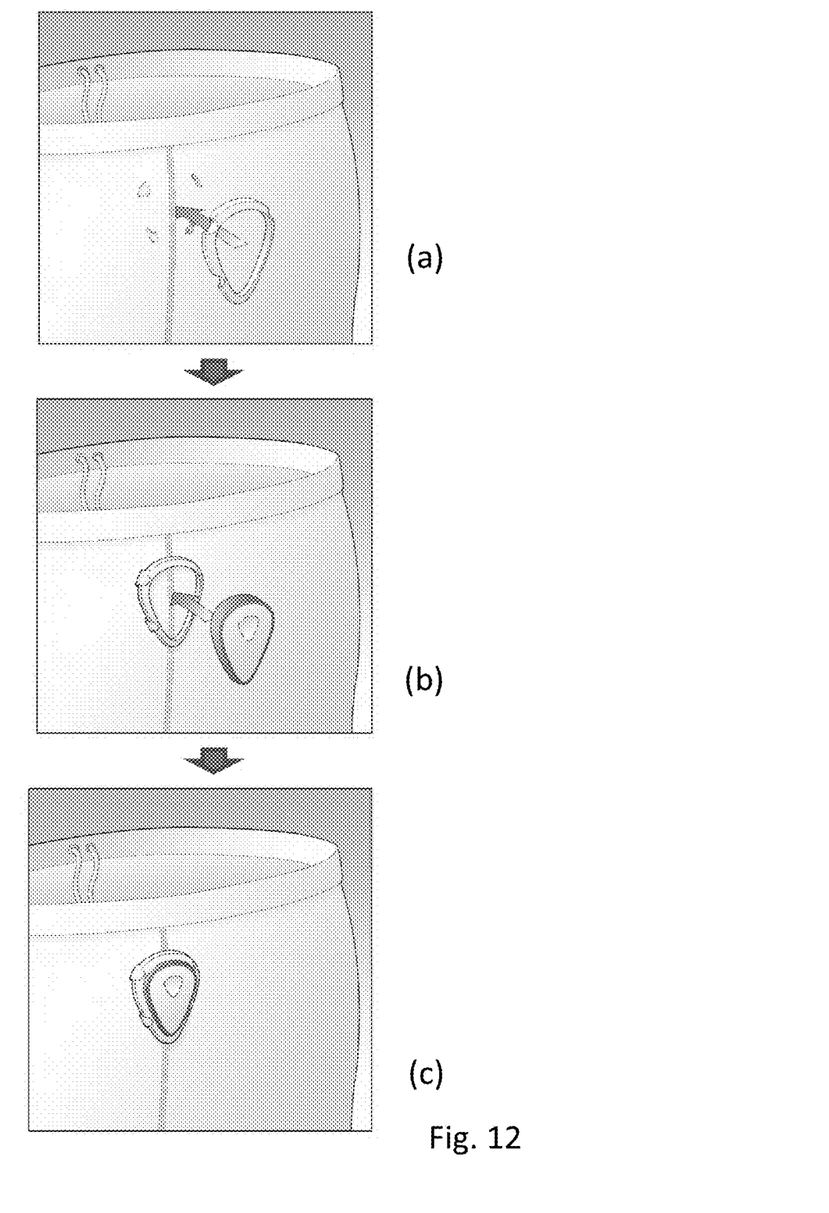

FIGS. 12(a) to (c) show a further arrangement for securing the activity monitor to a swimsuit. In this case, the activity monitor is mounted on the outside of the back of the swimsuit just below the waistband. The suit is formed with retaining tabs (seen in FIG. 12(a)) that are configured to engage and retain a mounting frame (seen in FIG. 12(b)). The activity monitor itself then clips into the mounting frame as seen in FIGS. 12(b) and (c).

Figure 9A:
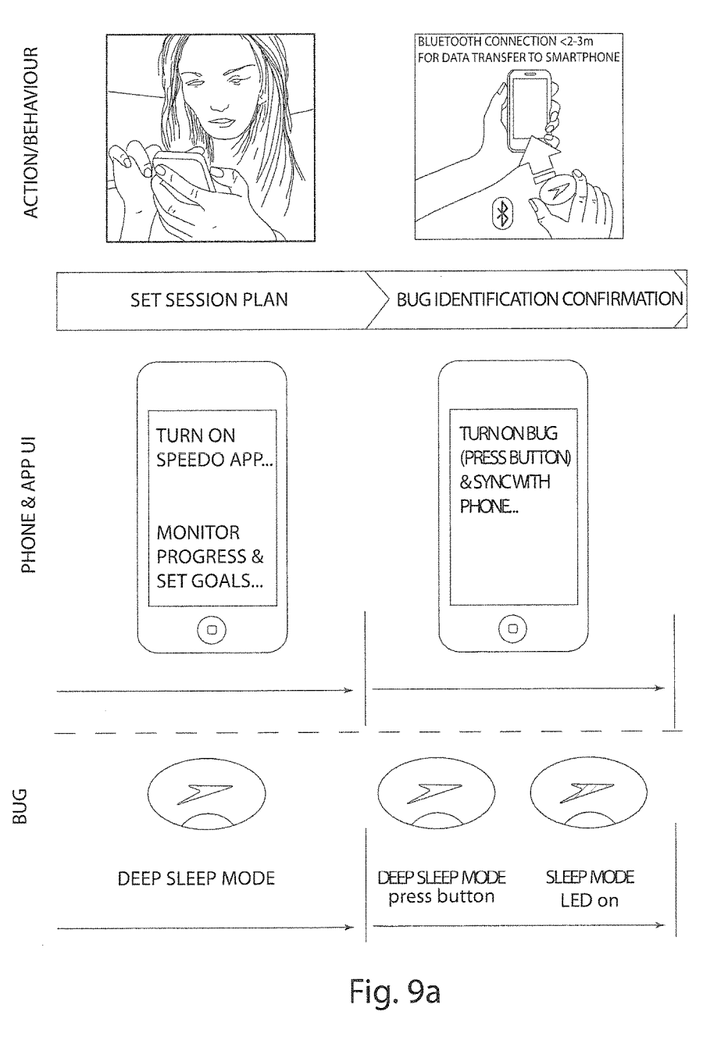
Figure 9B:
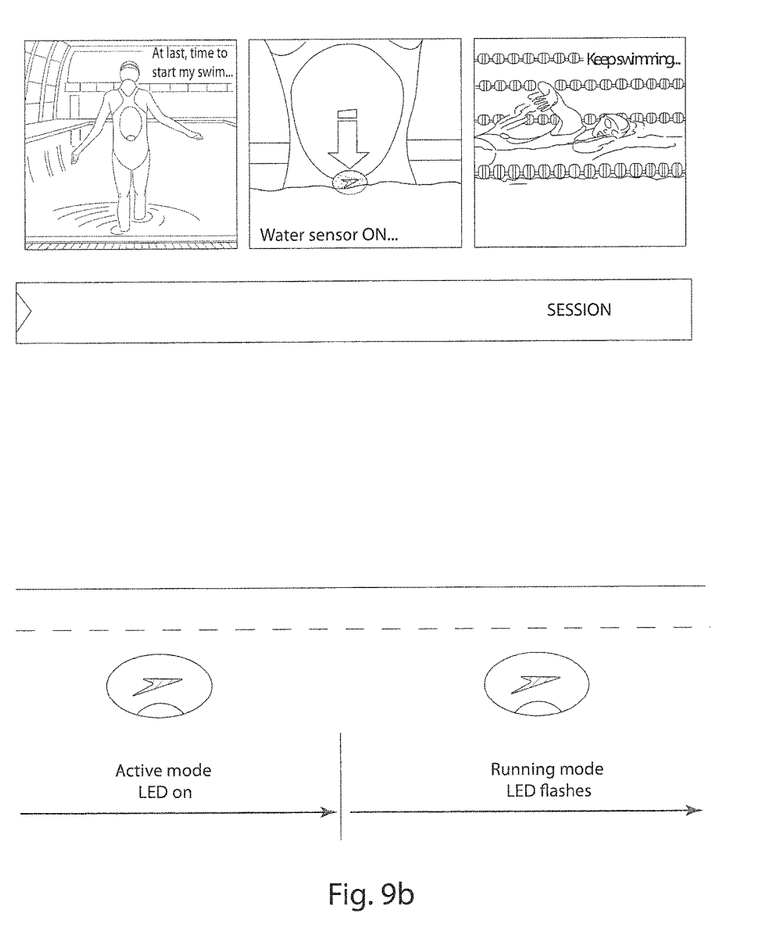
Figure 9C:
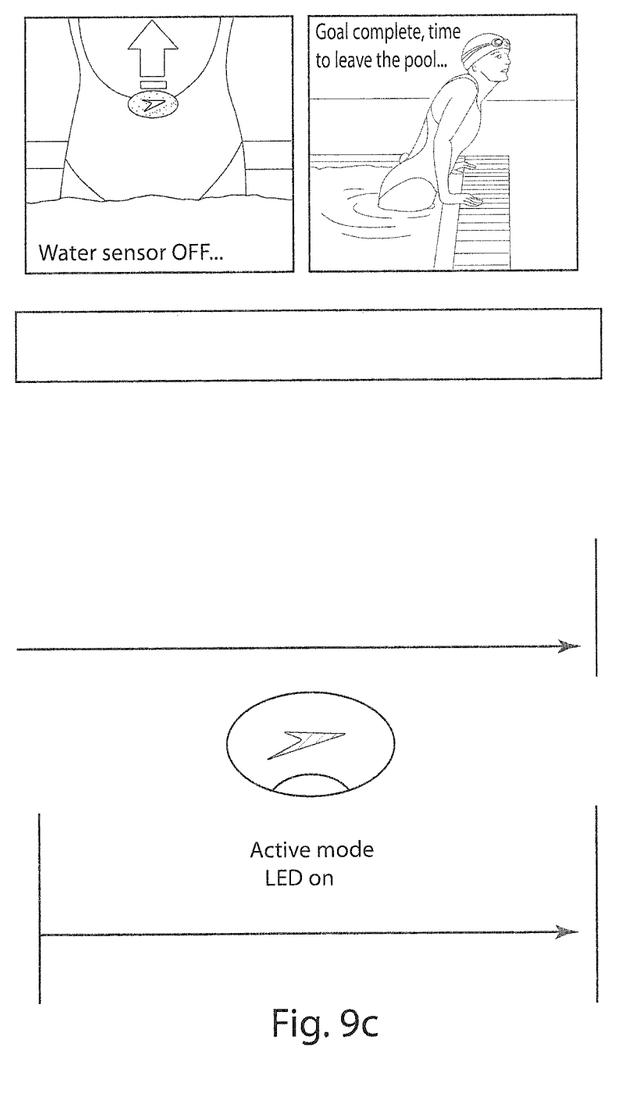
Figure 9D:
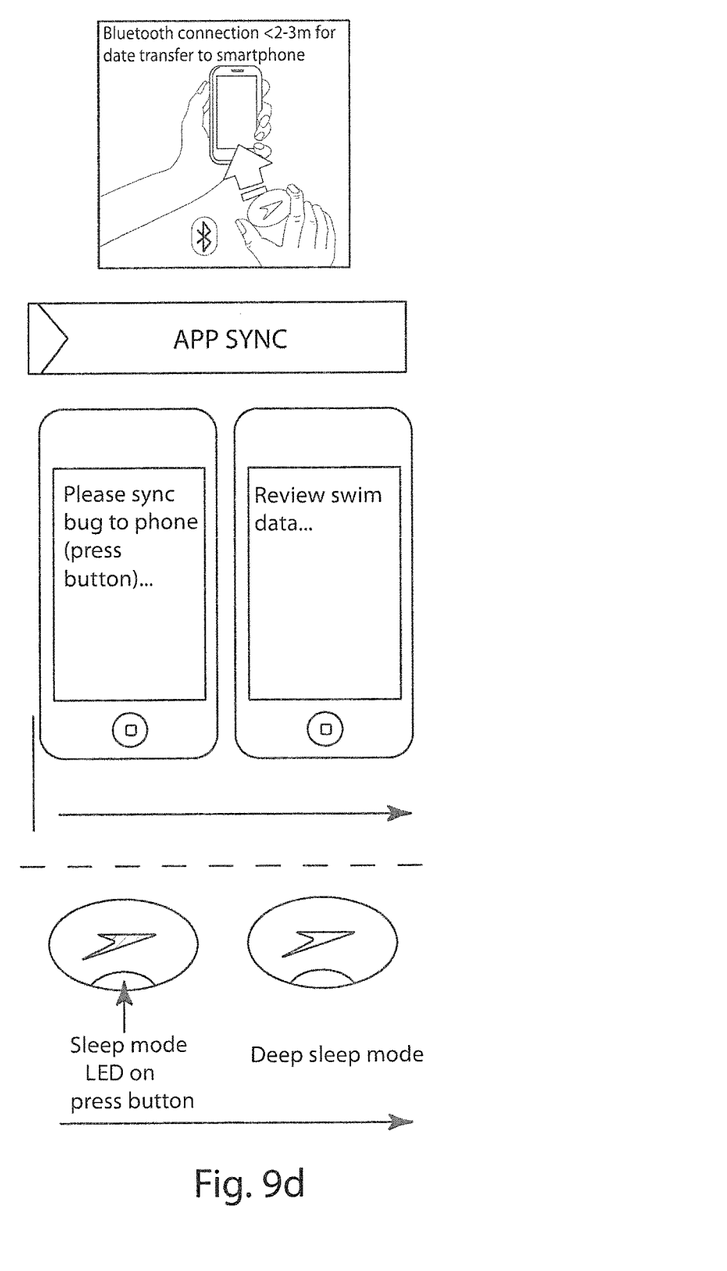

An example of the operation of the swim activity monitor to record a swim session will now be explained with reference FIGS. 9(a) to 9(b).

The user can start, if they wish, by setting goals using an app on their smartphone that later will receive data from the activity monitor. The app may have a record of data from previous swim sessions that the user can review to help with setting their goals for the upcoming session. The activity monitor is in a sleep mode at this point in time.

The user then triggers the monitor to switch from sleep mode to standby mode. This may, for example, be by some physical interaction with the monitor such as shaking it or pressing a button on the monitor, or it may be initiated with a command from the app on their smartphone sent to the activity monitor via a Bluetooth (or other wireless) connection.

Either before or after switching the monitor from sleep to standby mode, the user ensures the monitor is attached to their swimsuit at its predetermined location and in its correct orientation. The user then enters the pool and commences swimming, at which point the monitor automatically switches from standby mode to active mode. In this active mode the processor executes the algorithm to calculate and store to memory activity data based on output(s) from the motion/activity sensor(s).

When the swimmer completes their swim session and exits the pool, the water sensor detects that the monitor is no longer immersed and the activity monitor automatically switches from active mode back to standby mode. In some examples, if a user stops for a rest in the water, this can be detected (for example from the output of the motion sensor) and the monitor can be returned to standby mode until swimming commences again, even though the monitor is still immersed.

In standby mode, after the swim session has finished, the user can upload the activity data from the memory of the monitor to the app on their smartphone via the Bluetooth (or other wireless) connection. The user can then review this activity data and, if they wish, compare it with goals they have set and/or data from previous sessions.

The monitor is then returned to sleep mode, for example after a pre-determined period of time has elapsed without any activity (e.g. data communication, button press, etc) in standby mode (e.g. 30 mins). Additionally or alternatively, the activity monitor may be manually switched into standby mode, for example by pressing a button on the monitor or through an interface on their smartphone (or other computing device connected, e.g. wirelessly, to the activity monitor).

Various variations and modifications to the specifically described example are possible within the scope of the invention.

The invention claimed is:

1. An activity monitor for monitoring a water based activity performed by a user, the activity monitor comprising:
   a housing;
   at least one motion sensor;
   a processor;
   a battery to power the monitor; and
   a memory storing program code for execution by the processor to, in response to an indication of a first activation trigger, actuate a first switch in an operating state of the monitor from a sleep mode to a standby mode, and, in response to an indication of a second activation trigger that is different than the first activation trigger and comprises a detection of a predefined activity being performed by the user, actuate a second switch in the operating state of the monitor from the standby mode to an active mode in which the program code is further executed by the processor to calculate activity data based on an output from the at least one motion sensor that is indicative of activity performed by the user detected by the at least one motion sensor and to store the activity data in the memory, and
   wherein the monitor, when operating in the sleep mode, consumes low or no battery power, and
   wherein, when the monitor is operating in the standby mode, the monitor consumes battery power at a level that is higher than when operating in the sleep mode but the processor is not executing the program code to calculate and store the activity data such that operation of the monitor in the active mode in which the monitor consumes battery power at a level that is higher than when operating in the standby mode as a result of the processor executing the program code to calculate the activity data is restricted to periods of time following occurrences of the second switch being actuated in response to a detection of the predefined activity being performed by the user when the monitor is operating in the standby mode after the first switch having been actuated in response to an indication of the first activation trigger.

2. The activity monitor according to claim 1, wherein the first activation trigger is a detection of a physical interaction by the user with the monitor.

3. The activity monitor according to claim 1, wherein the first activation trigger is reception of a wireless signal from another device.

4. The activity monitor according to claim 1, further comprising a water sensor, and wherein the predefined activity comprises the user being in water and the detection of the predefined activity being performed by the user comprises an output from the water sensor that indicates that the monitor is immersed in water.

5. The activity monitor according to claim 1, wherein the predefined activity comprises at least one of the user being in water, the user being in a specified orientation, the user engaging in a specified movement, and the user initiating a manually-initiated trigger.

6. A method for recording water-based activity of a person wearing an activity monitor, the method comprising:
   in response an indication of a first activation trigger, actuating a first switch in an operating state of the activity monitor from a sleep mode in which a battery powering the monitor consumes little or no battery power to a standby mode in which the battery consumes battery power at a level that is higher than when the monitor is operating in the sleep mode;

upon receiving an indication of a detection of the activity monitor being immersed in water when the activity monitor is operating in the standby mode, automatically actuating a second switch in the operating state of the activity monitor from the standby mode to an active mode in which a processor of the activity monitor executes program code stored in a memory of the activity monitor to calculate activity data that is indicative of activity performed by the person detected by at least one sensor of the activity monitor; and upon receiving an indication of a detection of the activity monitor not being immersed in water when the activity monitor is operating in the active mode, automatically actuating a third switch in the operating state of the activity monitor from the active mode to the standby mode in which the processor is not executing the program code to calculate activity data, whereby operation of the activity monitor in the active mode in which the activity monitor consumes battery power at a level that is higher than when operating in the standby mode as a result of the processor executing the program code to calculate the activity data is restricted to periods of time following occurrences of the second switch being actuated in response to a detection of the activity monitor being immersed in water when the monitor is operating in the standby mode after the first switch having been actuated in response to an indication of the first activation trigger.

7. The method according to claim 6, wherein the second switch in the operating state of the activity monitor from the standby mode to the active mode is automatically actuated only upon the activity monitor being detected to be immersed in water and determining that an activity has commenced.

8. The method according to claim 6, wherein the processor of the activity monitor further executes the program code to record the activity data in the memory of the activity sensor when the activity sensor is operating in the active mode, and further comprising, after the third switch in the operating state of the activity monitor from the active mode to the standby mode being automatically actuated, transmitting the recorded activity data from the activity monitor to a computing device.

9. The method according to claim 7, wherein the activity monitor determines that an activity has commenced in response to at least one of a detected orientation of the person in the water and a detected movement of the person in the water by the at least one sensor.

10. The method according to claim 8, wherein prior to the person commencing the water-based activity, the computing device is operated to set one or more goals for the person, and upon a completion of the activity performed by the person being detected by the at least one sensor and transmission of the recorded activity data to the computing device, the computing device operates to compare the recorded activity data with the one or more goals that were set for the person.

* * * * *